(12) United States Patent
Morgan et al.

(10) Patent No.: US 8,091,555 B2
(45) Date of Patent: Jan. 10, 2012

(54) MOUTH GUARD

(75) Inventors: D. Scott Morgan, Indianapolis, IN (US); David L. Morgan, Indianapolis, IN (US)

(73) Assignee: D'Magination licensing and Servicing Company, LLC, Indianapolis, IN (US)

( * ) Notice: Subject to any disclaimer, the term of this patent is extended or adjusted under 35 U.S.C. 154(b) by 35 days.

(21) Appl. No.: 12/631,423

(22) Filed: Dec. 4, 2009

(65) Prior Publication Data

US 2010/0108078 A1 May 6, 2010

(51) Int. Cl.
*A61C 5/14* (2006.01)
(52) U.S. Cl. .................. 128/861; 128/859; 43/6
(58) Field of Classification Search .......... 128/859, 128/861–862; 602/902; 43/6
See application file for complete search history.

(56) References Cited

U.S. PATENT DOCUMENTS

| | | | |
|---|---|---|---|
| 3,385,291 A | 5/1968 | Martin | |
| 3,768,465 A | 10/1973 | Helmer | |
| 3,769,652 A | 11/1973 | Rainer | |
| 4,028,118 A | 6/1977 | Nakasuji et al. | |
| 4,044,762 A | 8/1977 | Jacobs | |
| 4,063,552 A | 12/1977 | Going et al. | |
| 4,495,945 A * | 1/1985 | Liegner | 128/200.26 |
| 5,051,476 A | 9/1991 | Uji | |
| 5,152,300 A | 10/1992 | Horst | |
| 5,620,011 A * | 4/1997 | Flowers | 128/859 |
| 5,682,904 A | 11/1997 | Stinnett | |
| 5,730,599 A * | 3/1998 | Pak | 433/215 |
| 6,318,371 B1 | 11/2001 | Tyszkiewicz | |
| 6,412,489 B1* | 7/2002 | Sue | 128/848 |
| 6,491,037 B1 | 12/2002 | Mortenson | |
| 6,886,567 B1 | 5/2005 | Liu | |
| 2003/0075184 A1 | 4/2003 | Persichetti | |
| 2003/0205234 A1 | 11/2003 | Bardach et al. | |
| 2004/0076219 A1* | 4/2004 | Madison et al. | 374/159 |
| 2004/0103905 A1 | 6/2004 | Farrell | |
| 2004/0154626 A1* | 8/2004 | Washburn et al. | 128/861 |
| 2004/0244805 A1 | 12/2004 | Cook et al. | |

* cited by examiner

*Primary Examiner* — Patricia Bianco
*Assistant Examiner* — Camtu Nguyen
(74) *Attorney, Agent, or Firm* — J. Stephen Wills; Alastair J. Warr; Kreig DeVault LLP

(57) ABSTRACT

Mouth guards of varying designs. The mouth guard is generally moldable and has non-planar biting surfaces. In other embodiments, the mouth guard has base members or flanges that have means for retaining medicaments and the like. Other versions have thermochromic elements selected to allow color changes at desired temperatures.

6 Claims, 11 Drawing Sheets

US 8,091,555 B2

MOUTH GUARD

RELATED APPLICATION

This application is related to, and claims the benefit of, U.S. patent application Ser. No. 11/113,513 entitled MOUTH GUARD, filed Apr. 25, 2005, which is incorporated herein by reference.

DETAILED DESCRIPTION OF VERSIONS OF THE INVENTION

Figure 1:
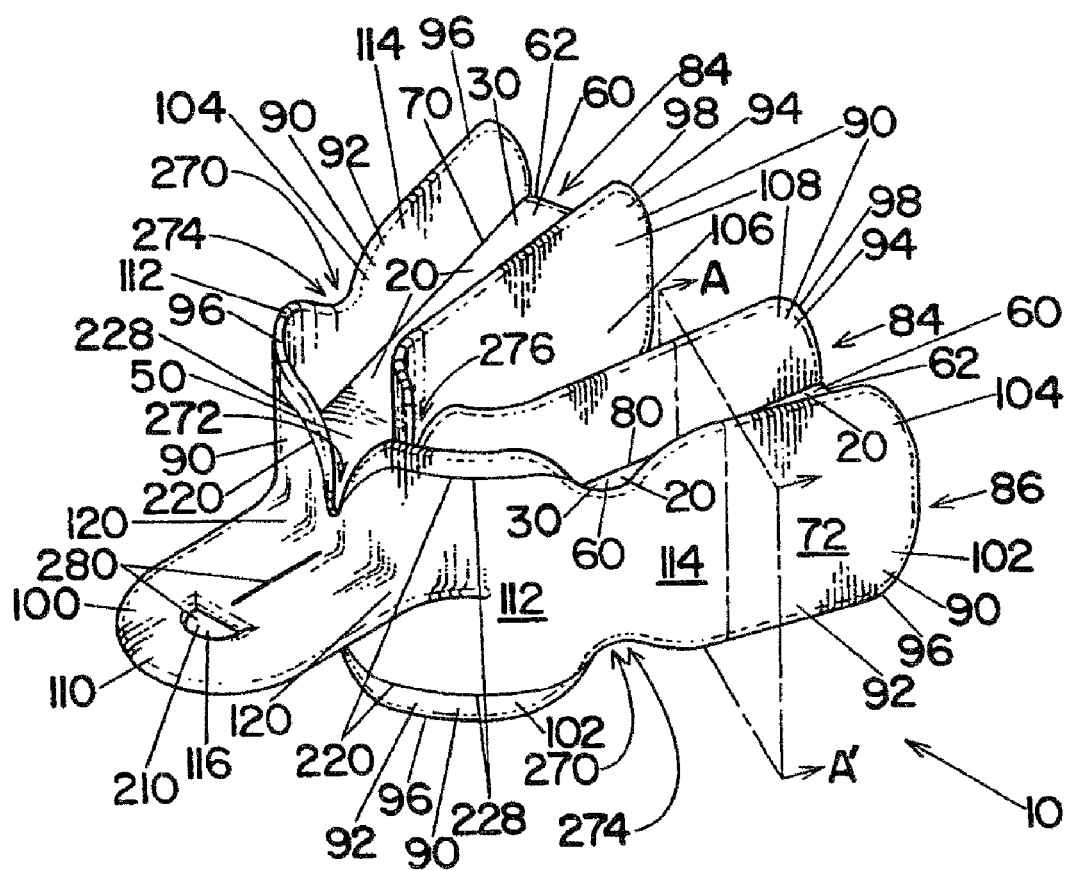
FIG. 1 is a perspective view of a first version of the mouth guard.

The mouth guard 10 for preventing oral tissue 232 injuries comprises a moldable base member 20 having first and second non-planar biting surfaces 30, 40 for positioning between occlusal tooth surfaces 230 of a user's upper and lower teeth 240, 250, the moldable base member 20, having an anterior portion 50, a posterior portion 60, a labial-buccal side 70, and a lingual side 80, and at least one moldable flange 90 extending from either the labial-buccal side 70 or the lingual side 80 of the moldable base member 20. The moldable flanges 90 can extend in a superior (upper) and/or inferior (lower) direction and are respectively shaped to form a barrier between a user's upper and lower teeth 240, 250 and a user's soft oral tissue 260.

Referring to FIG. 1, which shows a perspective view of one version of the mouth guard 10 having a generally arcuate shape. The moldable base member 20 of this version of the invention is the generally U-shaped portion comprising a first non-planar biting surface 30 and a second non-planar biting surface 40. The lingual side 80 defines the interior of the generally "U-shaped" moldable base member 20 that is proximate to the user's tongue. The labial-buccal side 70 defines the outer edge of the generally U-shaped moldable base member 20 that is proximate to the user's inner cheeks. The version in FIG. 1 has moldable flanges 90 attached to both the labial-buccal side 70 and lingual side 80. In one version, the moldable flanges 90 extend generally perpendicularly from the first non-planar biting surface 30 and the second non-planar biting surface 40.

In any disclosed version, a handle 100 can be affixed to the mouth guard 10 at the anterior portion 50. The posterior portion 60 defines generally that portion of the mouth guard 10 that is proximate to the user's molars when the mouth guard 10 is inserted into the user's mouth. The handle 100 has a distal end 110 and a proximate end 120. In one version, the proximate end 120 is affixed to the anterior portion 50 of the mouth guard 10. The handle 100 can be shaped and sized so that the distal end 110 extends out of the user's mouth. In some versions, the handle 100 has visual markings 280 to allow for proper alignment and positioning of the mouth guard 10 in the user's mouth. In other versions, the anterior portion 50 has visual markings 280 to allow for proper alignment and positioning of the mouth guard 10 in the user's mouth. In yet another version without a handle 100, the labial-buccal flange 92 has visual markings 280 to allow for proper alignment and positioning of the mouth guard 10 in the user's mouth. In one version, the central planar axis with which the handle 100 is aligned is substantially co-planar with the central planar axis upon which the moldable base member 20 is substantially aligned. In another version, the central planar axis of the handle 100 is substantially not co-planar with respect to the central planar axis of the moldable base member 20.

Figure 2:
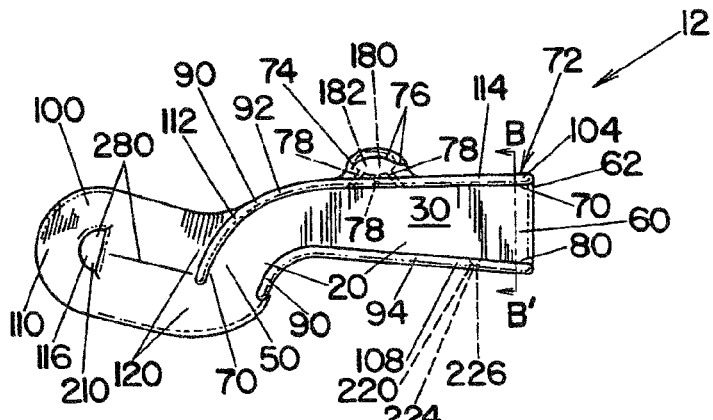
FIG. 2 is a top view of a second version of the mouth guard.

FIG. 2 shows a top view of a second version of the mouth guard 12 having a moldable base member 20 with a generally semi-arcuate shape. The moldable base member 20 forms a first non-planar biting surface 30, a second non-planar biting surface 40, a labial-buccal side 70, and a lingual side 80. The handle 100 extends from the anterior portion 50 or from the labial-buccal side 70. A tether retaining means, in the form of a hole 210, may be located in the distal end 110 of the handle 100. The flanges 90 attach to the moldable base member 20 at the sides 70, 80. Sectional plane A-A' exists on the mouth guard 10. The corresponding sectional lines B-B' and C-C' exist on mouth guards 12 and 14, respectively.

Figure 3:
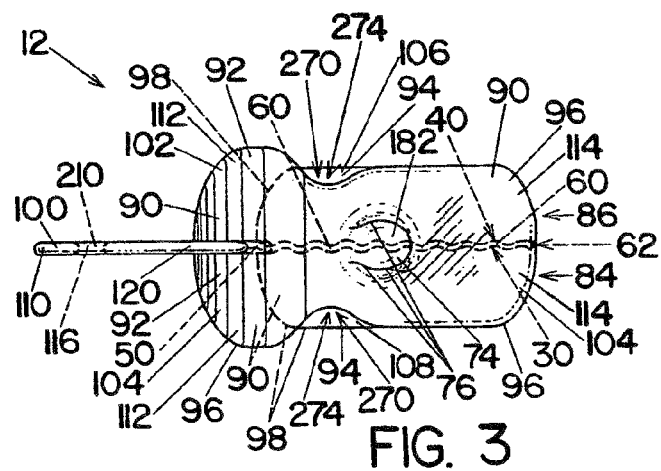
FIG. 3 is a buccal side view of the mouth guard shown in FIG. 2.

FIG. 3 shows a labial-buccal side view of the mouth guard 12. The moldable flanges 90 extend generally perpendicularly from the moldable base member 20. The moldable flanges 90 extend generally from either or both of the labial-buccal side 70 or the lingual side 80. The mouth guard 12 may have moldable flanges 90 extending away from either the first non-planar biting surface 30, or the second non-planar biting surface 40, or both the first non-planar biting surface 30 and the second non-planar biting surface 40. In yet other versions, the mouth guard 12 does not have flanges 90. The variations of the flanges 90 described with respect to the mouth guard 12 also apply to the mouth guard 10 (FIG. 1) and to the mouth guard 14 (FIGS. 16-18), and vice versa.

Figure 5:
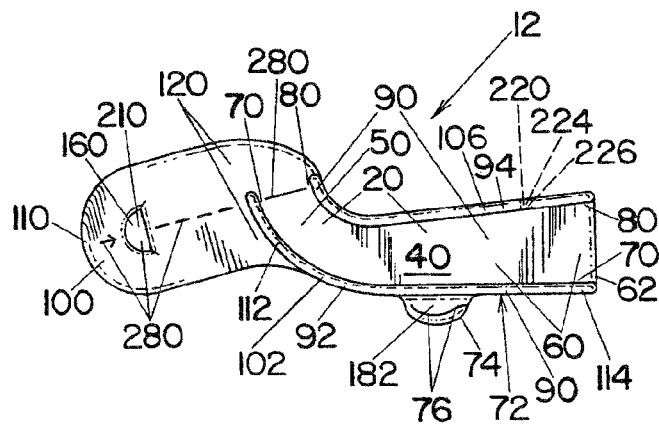
FIG. 5 is a bottom view of the second version of the mouth guard shown in FIG. 2.

The mouth guard 10 has a generally arcuate shape conforming to the general shape of a user's jaw to receive substantially all the user's upper teeth 240 and lower teeth 250. As shown in FIGS. 2 and 5, the mouth guard 12 comprises a generally semi-arcuate shape conforming substantially to the shape of one side of a user's jaw to receive substantially one side of the user's upper teeth 240 and one side of the lower teeth 250. One skilled in the art will appreciate that the scope of the disclosure and the appended claims includes other shapes and sizes of the mouth guard 10, 12, 14, so that it can be made to conform with all or only a portion of the teeth.

Referring to FIGS. 2, 3, 5, 13 and 14, the labial-buccal flange 92 can have incorporated onto its outer surface a retaining chamber 182 for containing and retaining a releasable flavoring substance or medication (not shown). The retaining chamber 182 is suitable for containing a small solid tablet or capsule. In one version (FIG. 3), the retaining chamber 182 comprises a bulge on the buccal surface 72 of the labial-buccal flange 92 of the mouth guard 10, 12, 14. The exterior wall 74 of the retaining chamber 182 is partially transected in one or more places by an elliptically shaped cut 76, which allows access to the retaining chamber 182, for placement of a flavoring substance or medication. The chamber 182 can be positioned anywhere on or in the mouth guard 10, 12, 14 without departing from the scope of the inventions disclosed and claimed.

The labial-buccal flanges 92 can have access tubules 78 within them that connect the retaining chamber 182 with the superior and inferior troughs 84, 86 of the mouth guard 10, 12, 14. The tubules 78 provide a means for delivering a medication directly to the teeth 240, 250 and gingiva 262.

Figure 6:
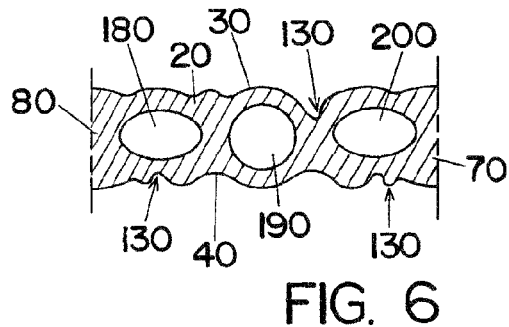
FIG. 6 is a cross-sectional view along sectional plane A-A' of the moldable base member having undulating, irregularly curved biting surfaces and a plurality of cavities.

Referring to FIG. 6, the moldable base member 20 can have a variety of shapes when viewed in cross-section. In the version shown in FIG. 6, the moldable base member 20 has one or more cavities 180, 190, 200. In other versions, the cavities 180, 190, 200 can provide means for positioning the mouth guard 10, 12, 14. In another version, the cavities 180, 190, 200 retain a flavoring substance. In yet another version, the cavities 180, 190, 200 retain a medication.

Figure 7:
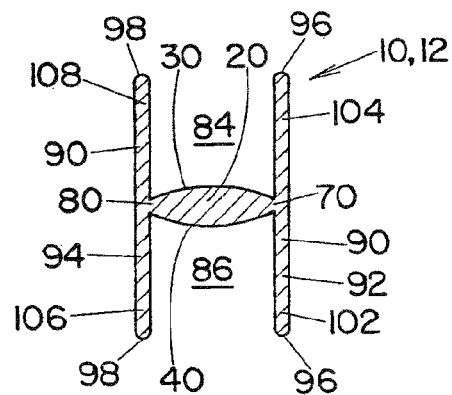
FIG. 7 is a cross-sectional view along sectional plane A-A' of a version of the mouth guard having generally convex non-planar biting surfaces.
Figure 8:
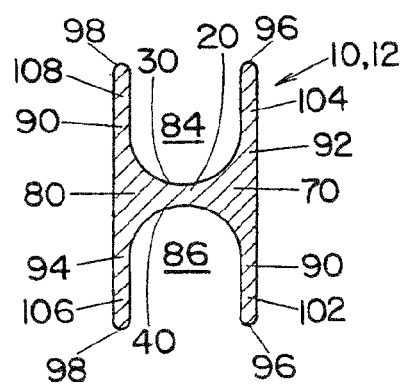
FIG. 8 is a cross-sectional view along sectional plane A-A' of a version of the mouth guard having generally concave non-planar biting surfaces.
Figure 9:
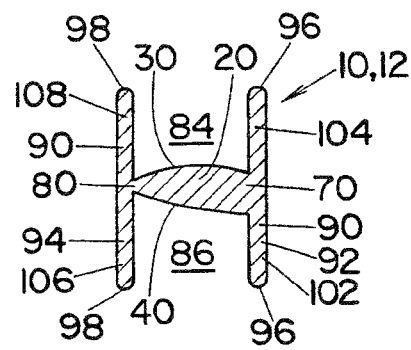
FIG. 9 is a cross-sectional view along sectional plane A-A' of a version of the mouth guard having curved biting surfaces of varying arc.

FIG. 7 shows a cross-sectional view of the mouth guard 10, 12, 14. The moldable base member 20 can have a generally convex or elliptical elevational cross-section along sectional plane A-A'. As shown in FIG. 8, which is a cross-sectional view of the mouth guard 10, 12, 14, the first and second non-planar biting surfaces 30, 40 can have a generally curved shape. As shown in FIG. 9, the first and second non-planar biting surfaces 30, 40 can have generally convex shapes with non-circular arcs of increasing or decreasing arc radius.

Figure 10:
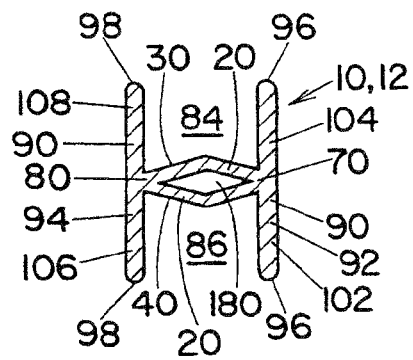
FIG. 10 is a cross-sectional view along sectional plane A-A' of a version of the mouth guard having chevron-shaped non-planar biting surfaces and a moldable base member with an internal cavity.
Figure 11:
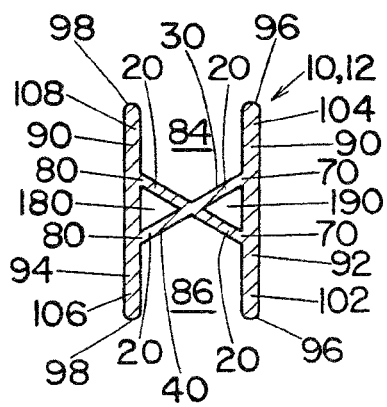
FIG. 11 is a cross-sectional view along sectional plane A-A' of a version of the mouth guard having "V-shaped" non-planar biting surfaces and a moldable base member with multiple internal cavities.
Figure 12:
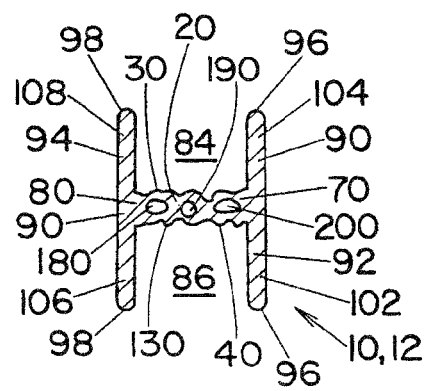
FIG. 12 is a cross-sectional view along sectional plane A-A' of another version of the mouth guard having irregularly deformed non-planar biting surfaces and a moldable base member with multiple internal cavities, as seen previously in FIG. 6.
Figure 13:
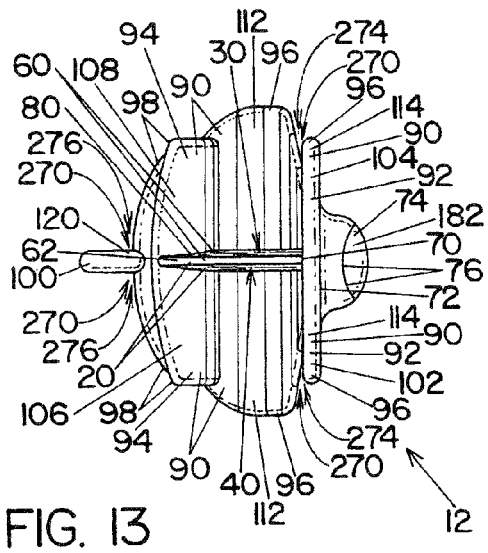
FIG. 13 is a posterior view of a third version of the mouth guard having a cavity or chamber.
Figure 14:
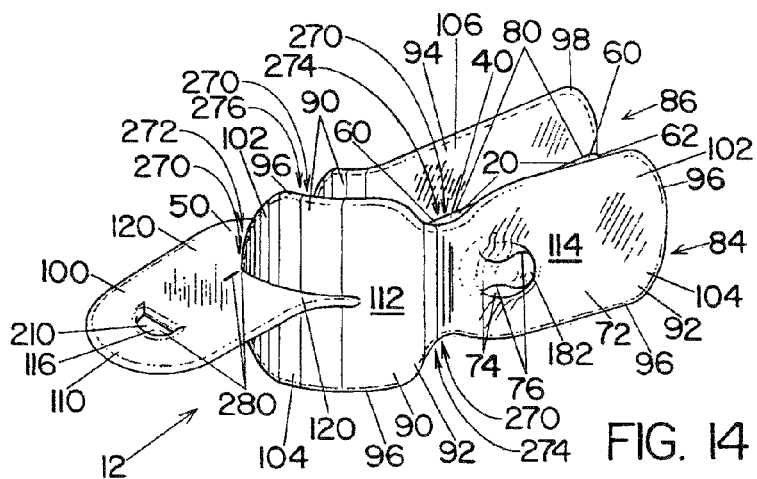
FIG. 14 is a perspective view of a third version of the mouth guard shown in FIG. 13 having a cavity or chamber.

As shown in FIGS. 10 and 11, the first and second non-planar biting surfaces 30, 40 can have a plurality of surfaces. In any of the mouth guards 10, 12, 14 the first and second non-planar biting surfaces 30, 40 can have a plurality of deformations 130, which may include, without limitation, ridges, ribs, waves, bumps, recesses, indents, grooves, furrows, dimples or any combination thereof. One skilled in the art will appreciate that the first and second non-planar biting surfaces 30, 40 can have any type of a combination of deformations 130 without departing from the scope of the described and claimed invention.

In some versions of the mouth guard 10, 12, 14, the moldable flanges 90 extend substantially parallel to each other from the labial-buccal and lingual sides 70, 80 at the anterior and posterior portions 50, 60 of the moldable base member 20 and generally perpendicularly to the first and the second non-planar biting surfaces 30, 40. In other versions, the moldable flanges 90 extend substantially from the labial-buccal and lingual sides 70, 80 at the anterior portion 50 of the moldable base member 20 generally perpendicular to the first and second non-planar biting surfaces 30, 40. In still other versions, the moldable flanges 90 extend substantially from the labial-buccal and lingual sides 70, 80 at the posterior portion 60 of the moldable base member 20 generally perpendicularly to the first and second non-planar biting surfaces 30, 40. In yet other versions, a moldable flange 90 extends generally from only the labial-buccal side 70 or from only the lingual side 80. In other versions, the moldable flanges 90 extend either substantially inferiorly or superiorly from either of the labial-buccal side 70 or the lingual side 80, or both, at one or more of the anterior or posterior portions 50, 60.

Figure 4:
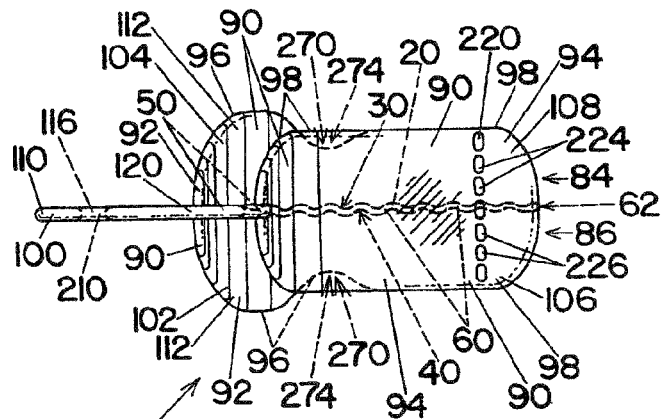
FIG. 4 is a lingual side view of the mouth guard shown in FIG. 2.

As shown in FIGS. 1, 3 and 4, in some versions of the invention, the moldable flanges 90 are shaped to conform to a plurality of frenae 140, 150, 160, 170 (shown in FIG. 32), which are variations of the soft oral tissue 260 that occur as natural anatomical features in the mouths of most people, by varying the distance that the moldable flanges 90 extend away from the moldable base member 20. This results in the formation of one or more frenal notches 270 in the flanges 90 that serve to increase the comfort of the device to the wearer by allowing room for the frenae. In one version, the moldable flanges 90 are made to conform to the maxillary labial-buccal frenae 150. In another version, the moldable flanges 90 are made to conform to the mandibular labial-buccal and lingual frenae 160, 170. If the initial shapes of the flanges 90 do not adequately conform to the shape of the person's soft oral tissues 260, then the edges 96, 98 of the labial-buccal and lingual flanges 92, 94 can be shaped appropriately with scissors 204 or other means as shown in FIG. 16.

The mouth guard 10, 12, 14 can have size adjusting means 220. One version of the size adjusting means 220, shown in FIGS. 16 through 19, is comprised of a series of slots 224 that pass through the moldable base member 20. The size adjusting means 220 can comprise one or more perforations 226, indentations, grooves, scoring lines 228, ridges or any combination thereof, in the first and second non-planar biting surfaces 30, 40, the moldable base member 20 and/or the moldable flanges 90. In other versions, the size adjusting means 220 is comprised of one or more visual markings 280 suitable for allowing portions of the mouth guard 10 to be removed selectively to size the mouth guard 10, 12, 14 as desired. The visual markings 280 can serve several purposes. For example, the markings 280 can be positioned on the handle 100 or the anterior portion 50 to allow for proper positioning of the mouth guard 10, 12, 14 relative to anatomical features of the user, such as the philtrum 290. Alternatively, the visual markings 280 can be selectively positioned on the flanges 90 to serve as a guide to allow for selective sizing of the mouth guard 10, 12, 14.

Figure 15:
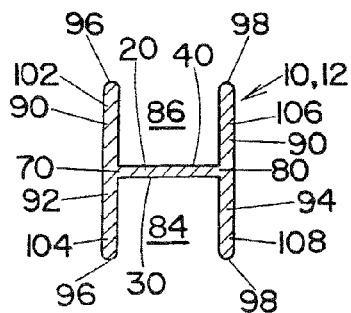
FIG. 15 is a cross-sectional view along sectional plane B-B' of one version of the mouth guard having non-planar biting surfaces.

As shown in FIGS. 7-12, if a cross-section of the mouth guard 10 is taken along sectional plane A-A' (or sectional line B-B' as for mouth guard 12, or sectional line C-C' for mouth guard 14), which is perpendicular to the longitudinal midline of the moldable base member 20, then some versions of the mouth guard 10, 12, 14 have a generally "H-shaped" configuration. This can be seen most clearly in the cross-sectional drawing shown in FIG. 15, which shows the cross-section that results from a section taken along sectional line B-B' in FIG. 2. One skilled in the art will understand that the mouth guard 10, 12, 14 may be manufactured with a cross-section that shows from zero to four moldable flanges 90. The labial-buccal flange 92 forms one of the vertical sides of the generally "H-shaped" configuration and can be subdivided at its point of connection to the moldable base member 20 into two flanges that form its inferior and superior portions 102, 104. The lingual flange 94 forms the other vertical side of the "H-shaped" cross-section. The lingual flange 94 can also be subdivided at its point of connection to the moldable base member 20 into two flanges thus forming its inferior and superior portions 106, 108. The moldable base member 20 extends between the flanges 92, 94.

Figure 16:
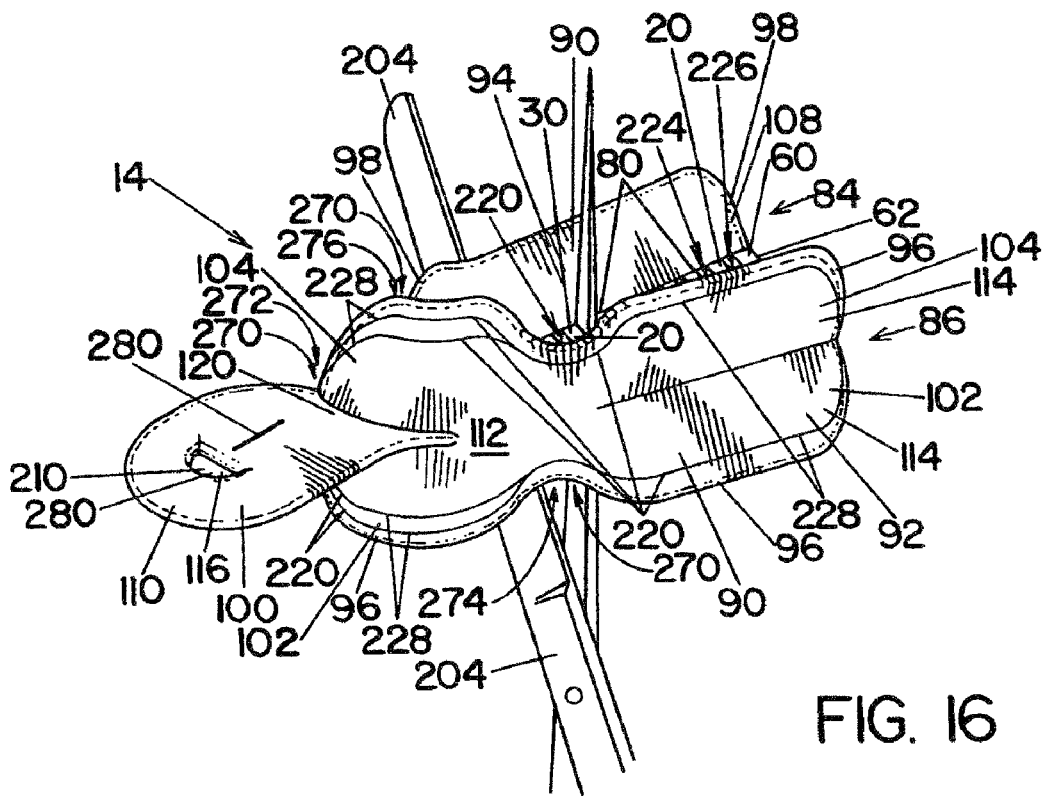
FIG. 16 is a perspective view of another version of the mouth guard with a base member and labial-buccal and lingual flanges that can be sized to accommodate small mouths.

FIG. 16 shows a perspective view of the mouth guard 14 in which the labial-buccal and lingual flanges 92, 94 are slightly angled to conform more correctly with the natural anatomical form of the upper and lower jaws, while still maintaining a position that is generally perpendicular to the moldable base member 20. The change in the position of the flanges 90 in this version is seen most clearly in FIG. 17, which is a top view of the device shown in FIG. 16, and is fabricated by changing the angulations of the labial-buccal and lingual flanges 92, 94 as follows. The free edge 98 of the lingual flange 94 is positioned more lingually (interiorly) relative to its point of attachment to the moldable base member 20, giving the lingual flange a slight lingual (inward) tilt. The anterior, or labial portion 112, of the labial-buccal flange 92 is also given a slight lingual (inward) tilt by positioning the free edge 96 of the labial-buccal flange 92 more lingually (interiorly) relative to its point of attachment to the moldable base member 20. The posterior, or buccal portion 114, of the labial-buccal flange 92 is given a slight buccal (outward) tilt by positioning the free edge 96 of the labial-buccal flange 92 more buccally (exteriorly) relative to the flanges 92 point of attachment to the moldable base member 20.

Figure 17:
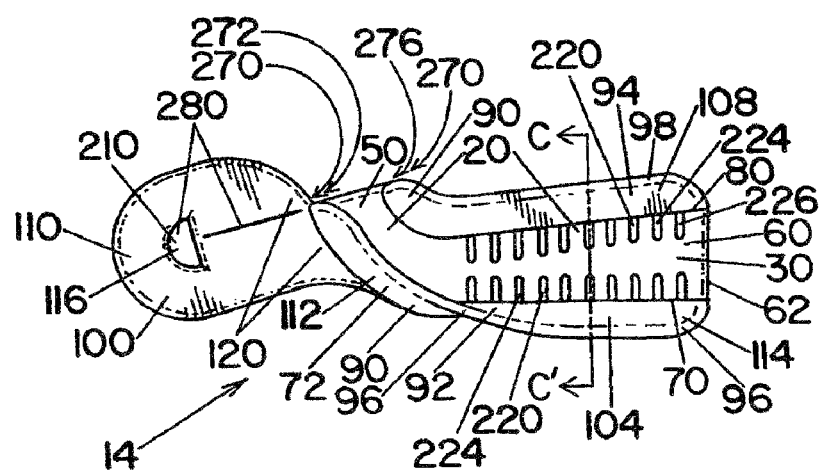
FIG. 17 is a top view of the version of the mouth guard shown in FIG. 16.

FIGS. 16-19 show various views of an anatomically corrected version of the mouth guard 14, along with a size adjusting means 220, which allows for adjustment of the anterior-posterior length of the moldable base member 20, as well as the moldable flanges 90 at multiple corresponding points. The size adjusting means 220 consists of multiple sets of spaced apart slots 224 that pass through the moldable base member 20 and are seen best in the cross-sectional view of the mouth guard 10, 12, 14 in FIG. 19. The slots 224 project generally perpendicularly toward the longitudinal midline of the moldable base member 20 away from both the labial-buccal and lingual sides 70, 80 of the moldable base member 20. The lengths of the slots 224 being generally perpendicular to the longitudinal midline of the moldable base member 20, but not so long that the slots 224 along one side of the midline of the moldable base member 20 cross over the midline and become connected to the slots 224 along the other side, as seen in FIG. 17. Thus, the moldable base member 20 remains intact along its longitudinal midline.

Other size adjusting means 220 may include, but are not limited to, lines, dashes, markings, ridges, perforations, partial perforations, intermittent perforations, continuous or intermittent scoring 228 or other indicia as a means of indicating a desirable point of adjustment or separation. By way of example, FIG. 4 illustrates a lingual flange 94 with size adjusting means 220 consisting of intermittent perforations 226 aligned in an inferior-superior direction, which indicates the most desirable single point of adjustment. The mouth guard 10, 12, 14 can be fabricated without markings, thus leaving an individual to make any adjustments to the size of the mouth guard that are deemed necessary.

Figure 32:
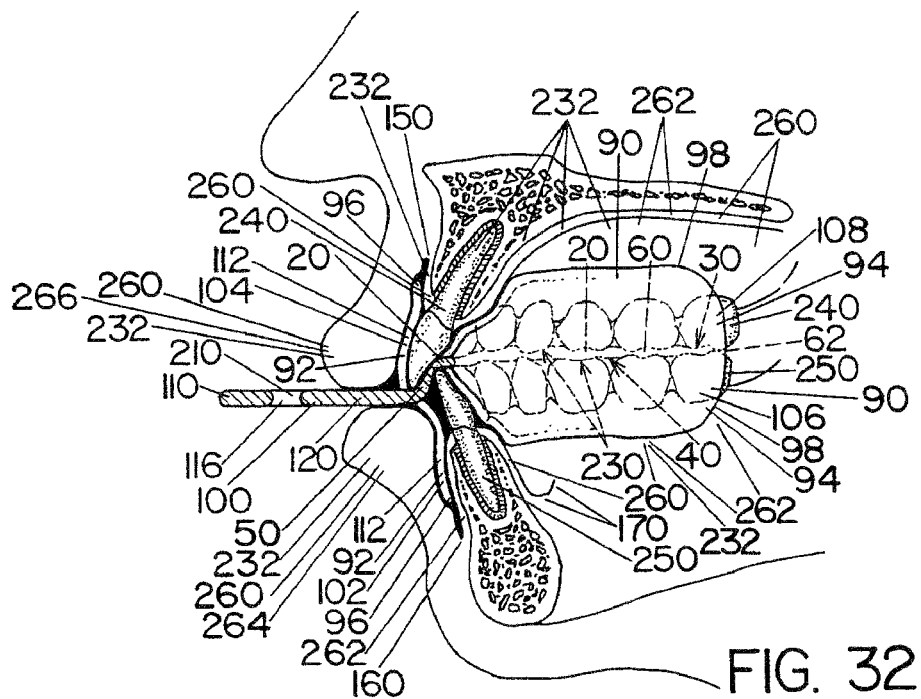
FIG. 32 is a mid-sagittal cross-sectional view of the mouth guard shown in FIG. 1 positioned in a user's mouth.

The inferior-superior dimensions of the moldable flanges 90 may be made to vary in distance away from the moldable base member 20 to accommodate the oral tissues, including the frenae 150, 160, 170 (shown in FIG. 32). The dimensions of the superior portions 104, 108 and the inferior portions 102, 106 of the moldable flanges 90 will be substantially the same on either the labial-buccal flange 92 or the lingual flange 94, or both. The flanges 90 are integral with and connected to the moldable base member 20 at its sides 70, 80, which creates a cross-section of the moldable base member 20 and the moldable flanges 90 that is an inferior-superior mirror image around the moldable base member 20. The flanges 90 may have one or more cavities 180, 190. As one skilled in the art will recognize, the term superior refers to the upper part of the guard 10, 12, 14 and the term inferior means the lower part of the guard 10, 12, 14.

In certain versions of the invention, the mouth guard 10, 12, 14 has a total lingual flange 94 width from the inferior most point to the superior most point that is about 18 to about 30 mm. The total labial-buccal flange 92 width of the mouth guard 10, 12, 14 can vary from its inferior most point to its superior most point. The narrowest dimension is located at either the labial frenal notch 272 or the lingual frenal notch 276, which is preferably about 6 mm, or less, to about 18 mm wide from its inferior most point to its superior most point. At the buccal frenal notch 274, the width is about 12 mm to about 25 mm wide from the inferior most point to the superior most point. In one version, the widest dimension of the labial-buccal flange 92 is about 24 mm to about 36 mm. In another version, the width of the posterior, buccal portion 114, of the labial-buccal flange 92 is about 18 mm to about 30 mm.

The width of the moldable base member 20 and the corresponding distance between the flanges 94 and 92 varies along the length of the first and second non-planar biting surfaces 30, 40. This distance between the flanges 92, 94 has practical limits that are generally established by the average range of sizes of the teeth, jaws, gums and bones. The first and second non-planar biting surfaces 30, 40, along with the corresponding moldable base member 20 are narrower at the anterior portion 50 than at the posterior portion 60. In some versions, the absence of vertical end walls (not shown) at the posterior edge 62 of the posterior portion 60 of the moldable base member 20 facilitates forming the mouth guard 10, 12, 14 into a few standard sizes, which fit all or almost all teeth in most jaws, upper jaws as well as lower jaws, without any major adjustments needed for the mouth guard 10, 12, 14.

The width, that is the distance from the labial-buccal side 70 to the lingual side 80 of the moldable base member 20, in the anterior portion 50, is from about 4 mm to at least about 12 mm or more. In one version, the width at the anterior portion 50 is about 8 mm. This width gradually increases towards the posterior portion 60 of the moldable base member 20, which is from about 8 to about 20 mm. In one version, the width at the posterior portion 50 is about 14 mm.

In versions suitable for children, the moldable base member 20 has a width in the anterior portion 50 of from about 4 mm to at least about 12 mm. In one version, the width at the anterior portion 50 is about 8 mm. This width gradually increases towards the posterior portion 60 to be from about 6 mm to about 14 mm. In one version, the increased width at the posterior portion 60 is about 10 mm.

Figure 18:
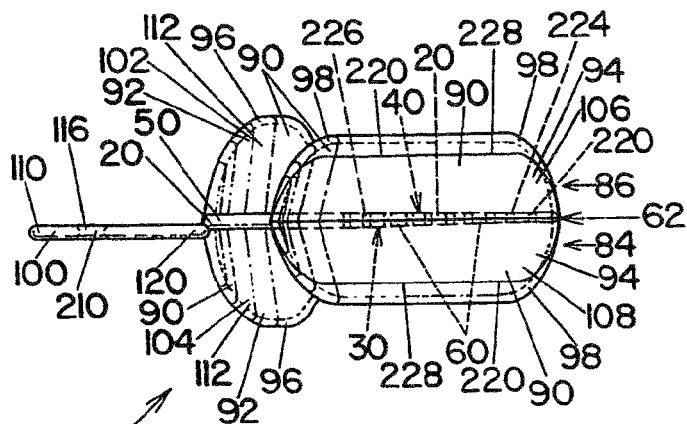
FIG. 18 is a lingual side view of the version of the mouth guard shown in FIGS. 16 and 17.

Referring to FIG. 18, the handle 100 may be offset in an inferior-superior direction from the moldable base member 20. As can be seen in this lingual side view, the handle 100 has become an extension of the mouth guard 10 off of the labial-buccal flange 92. This is further illustrated in the top view, FIG. 17, in which the handle 100 is shown to attach via its proximate end 120 to the labial-buccal flange 92.

In one version, the handle 100 is from about 19 mm to about 25 mm wide. The handle 100 in some versions is designed to protrude out of the mouth and beyond the front of the lips 264 a minimum distance of about 10 mm to 20 mm, or more. A distance of about 10 mm is the minimum amount necessary for a responsible person, such as a caretaker, to effectively make use of the handle 100 to adjust its position without placing a finger, or fingers, inside of the mouth. The hole 210 can be about 6 mm to about 12 mm in width or diameter.

Referring to FIGS. 1, 2, 5, 14, 16, 17, and 33, the mouth guard retaining means 116 of the present invention is embodied in the combination of a tether 118 (shown in FIG. 33) that is passed through a hole 210. The hole 210 can be sized to approximately the same width as an average sized philtrum 290 of the upper lip 266, which is from about 8 mm to about 12 mm for adults. The hole 210 can be positioned a minimum of about 15 mm from the anterior portion 50.

Figure 19:
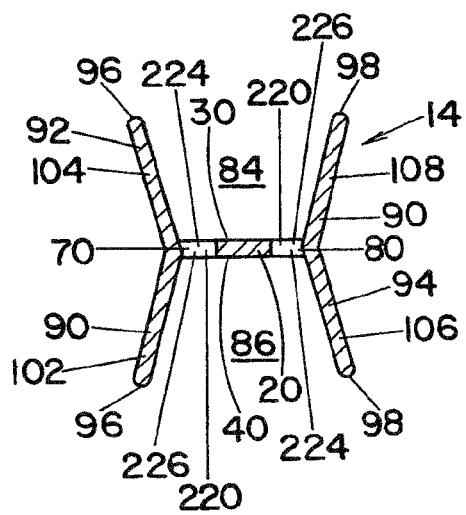
FIG. 19 is a cross-sectional view along sectional line C-C' of the mouth guard shown in FIG. 17.
Figure 20:
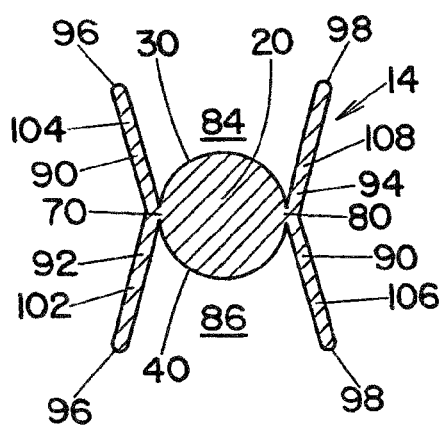
FIG. 20 is a cross-sectional view along sectional line C-C' of another form of the mouth guard shown in FIG. 17 having semi-circular non-planar biting surfaces with a moldable base member that is solid internally.

The cross-sectional views of FIGS. 19-31 illustrate the multiplicity of shapes into which the moldable base member 20 can be formed. FIG. 19 shows a cross-sectional view of FIG. 17 taken along sectional line C-C' where the flanges 90 are generally perpendicular to the base member 20. In the version shown in FIG. 20, the moldable base member 20 can have a generally solid, circular elevational cross-section.

Figure 21:
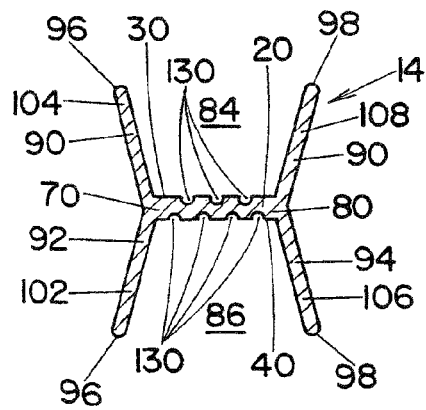
FIG. 21 is a cross-sectional view along sectional line C-C' of the mouth guard shown in FIG. 17 having dimpled non-planar biting surfaces.

FIG. 21 shows a moldable base member 20 with multiple deformations 130 in the form of indentations or dimples, upon its first and second non-planar biting surfaces 30, 40.

Figure 22:
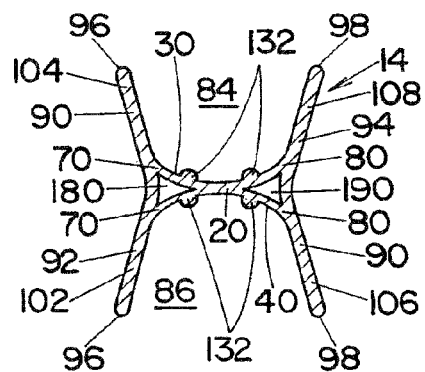
FIG. 22 is a cross-sectional view along sectional line C-C' of the mouth guard shown in FIG. 17 having concave non-planar biting surfaces with multiple bumps and a moldable base member that has multiple internal cavities.

As shown in FIG. 22, the moldable base member 20 has one or more cavities 180, 190 that underlie its bump 132 bearing, concave shaped, first and second non-planar biting surfaces 30, 40.

Figure 23:
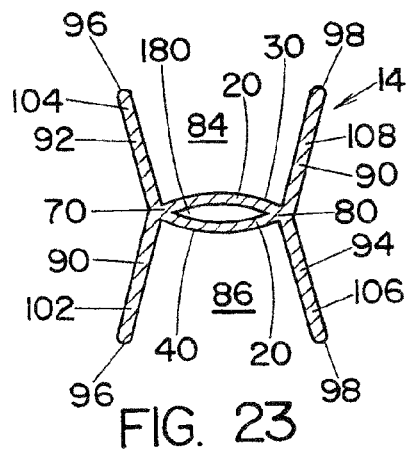
FIG. 23 is a cross-sectional view along sectional line C-C' of the mouth guard shown in FIG. 17 having curved non-planar biting surfaces with a moldable base member that has an internal cavity.

The moldable base member 20 shown in FIG. 23, has generally convex first and second non-planar biting surfaces 30, 40 that overlie a cavity 180 which can be used to hold a medication or a flavoring substance.

Figure 24:
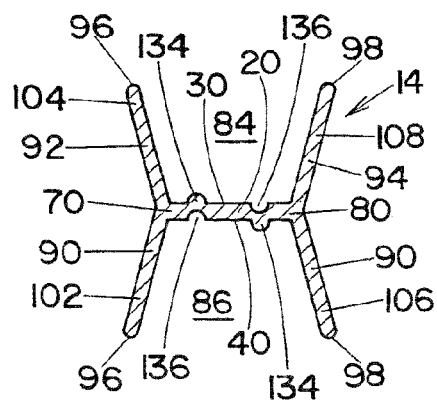
FIG. 24 is a cross-sectional view along sectional line C-C' of the mouth guard shown in FIG. 17 having non-planar biting surfaces, which contain ridges and furrows that run parallel to the longitudinal midline of the moldable base member.

FIG. 24 illustrates a moldable base member with first and second non-planar biting surfaces 30, 40 that have alternating ridges 134 and furrows 136 running parallel to the longitudinal axis of the moldable base member 20.

Figure 25:
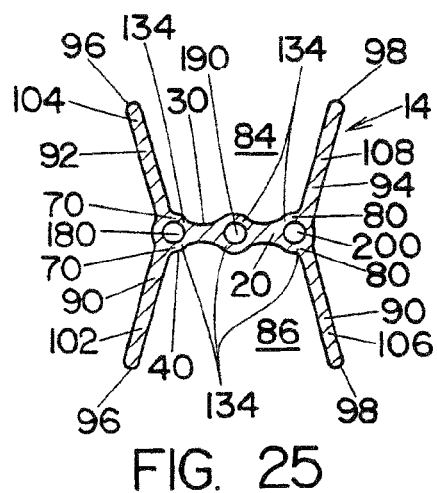
FIG. 25 is a cross-sectional view along sectional line C-C' of the mouth guard shown in FIG. 17 having multiple-ridged non-planar biting surfaces with a moldable base member that has multiple internal cavities.

As shown in FIG. 25, the moldable base member 20 has first and second non-planar biting surfaces 30, 40 with multiple ridges 134 running parallel to the longitudinal axis of the moldable base member 20 with multiple corresponding cavities 180, 190, 200 deep to the ridge formations.

Figure 26:
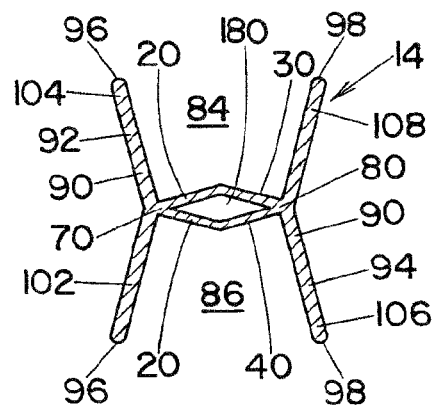
FIG. 26 is a cross-sectional view along sectional line C-C' of the mouth guard shown in FIG. 17 having a diamond shaped moldable base member with chevron-shaped non-planar biting surfaces and an internal cavity.

The moldable base member 20 illustrated in FIG. 26 is a hollow diamond shape, which is similar in form to that shown in FIG. 10, yet with thinner base member 20 thickness between the cavity 180, and the first and second non-planar biting surfaces 30, 40.

Figure 27:
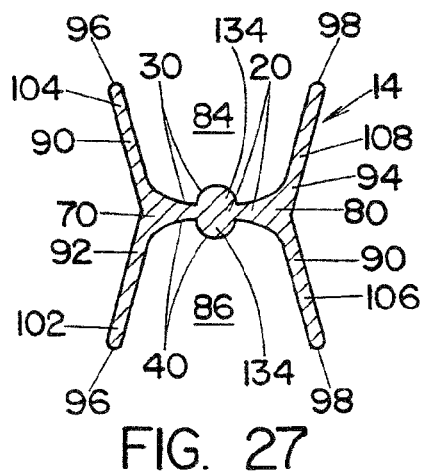
FIG. 27 is a cross-sectional view along sectional line C-C' of the mouth guard shown in FIG. 17 having non-planar biting surfaces, which have a single ridge running along the longitudinal midline of the moldable base member that is solid internally.

As shown in FIG. 27, the first and second non-planar biting surfaces 30, 40 of the moldable base member 20 are concave and have at least one ridge 134 that runs along with, or parallel to, the longitudinal midline of the moldable base member 20. Additionally, there is no cavity that runs deep to a ridge 134 in this version of the moldable base member 20.

Figure 28:
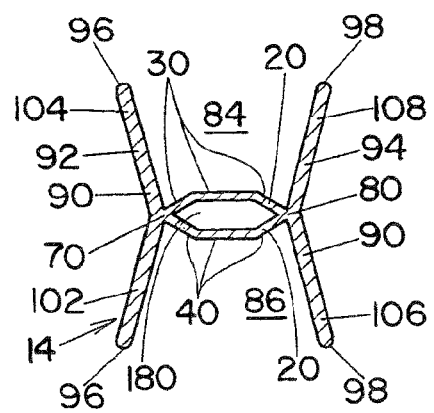
FIG. 28 is a cross-sectional view along sectional line C-C' of the mouth guard shown in FIG. 17 having a hexagonally shaped moldable base member, which has multi-planar biting surfaces and an internal cavity.

FIG. 28 illustrates a moldable base member 20, which is hexagonal in cross-section and has one or more cavities 180.

Figure 29:
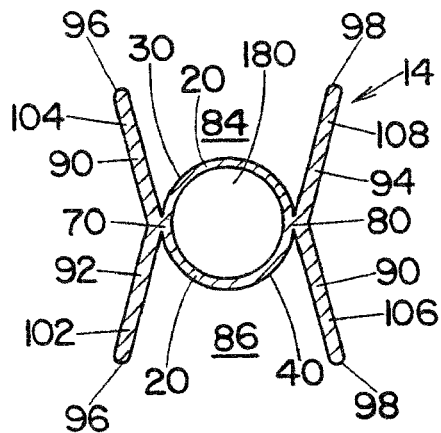
FIG. 29 is a cross-sectional view along sectional line C-C' of the mouth guard shown in FIG. 17 having semi-circular non-planar biting surfaces with a moldable base member that has an internal cavity.

The version of the moldable base member 20 revealed in FIG. 29 shows that it can have a generally hollow circular elevational cross-section, which contains a cavity 180.

Figure 30:
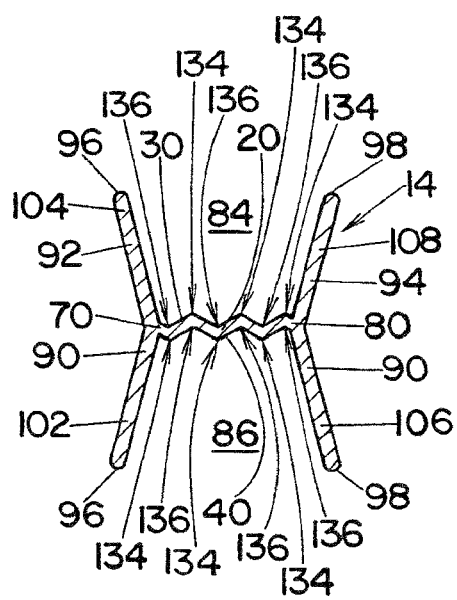
FIG. 30 is a cross-sectional view along sectional line C-C' of the mouth guard shown in FIG. 17 having multi-planar ridges as its non-planar biting surfaces.

The moldable base member 20 shown in FIG. 30 has several longitudinally arranged, sharply peaked/terminating ridges 134 and furrows 136 that alternate from side to side resulting in a moldable base member 20 that has a zigzag appearance when it is viewed in cross-section.

Figure 31:
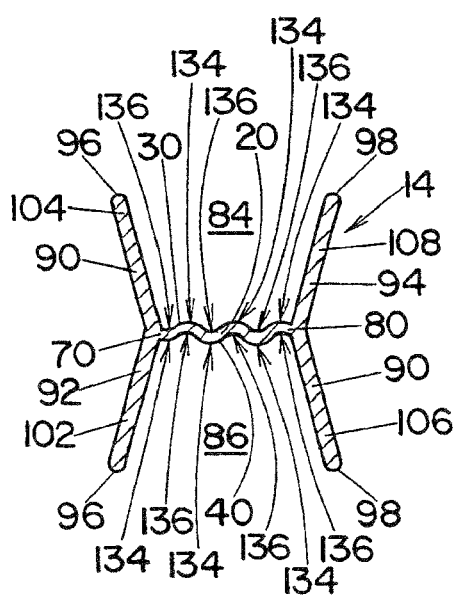
FIG. 31 is a cross-sectional view along sectional line C-C' of the mouth guard shown in FIG. 17 having multi-ridged non-planar biting surfaces.

The moldable base member 20 of FIG. 31 is similar to that of FIG. 30 in that it has several longitudinally arranged, but rounded, ridges 134 and furrows 136, which result in a wave-like appearance when viewed in cross-section.

FIG. 32 is a cross-sectional, mid-sagittal view of the mouth guard in proper protective position in the mouth of a user. The first non-planar biting surface 30 engages occlusal tooth surfaces 230 of the upper teeth 240. The second non-planar biting surface 40 engages occlusal tooth surfaces 230 of the lower teeth 250. The moldable flanges 90 are essentially and substantially shaped to mold to the forms of the frenae 150, 160, 170 and to cover the teeth 240, 250 and the gingiva 262 adjacent to the teeth 240, 250.

Figure 33:
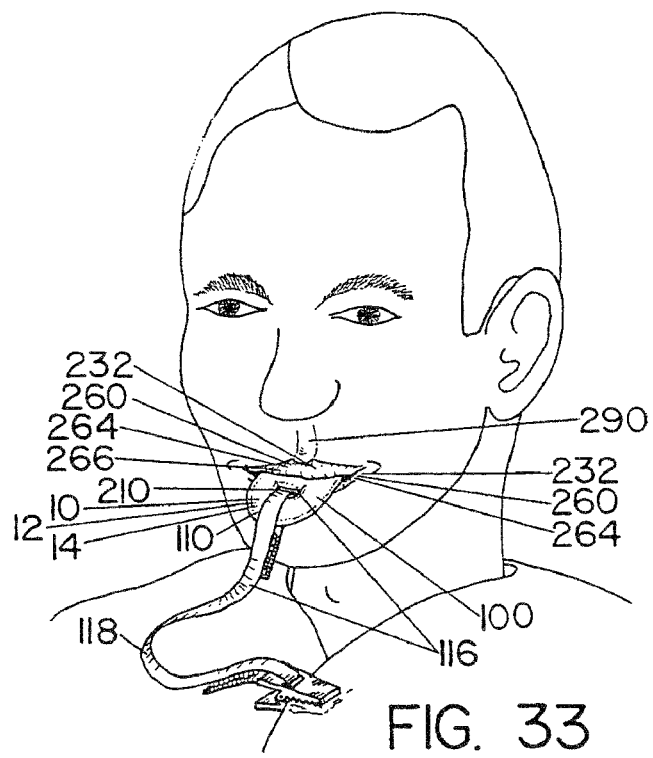
FIG. 33 is a perspective view of a person with the mouth guard shown in FIG. 1 placed in the mouth.

FIG. 33 shows a perspective view of a person with a version of the mouth guard 10, 12, 14 of the present invention in their closed mouth in the proper protective position. The handle 100 is seen to project out of the mouth between the lips 264. A portion of the mouth guard retaining means 116 in the form of a hole 210, in the handle 100 is aligned with the philtrum 290 of the upper lip 266, thus confirming that the placement of the mouth guard 10, 12, 14 within the oral cavity is correct. A second portion of a mouth guard retaining means 116 is also shown in FIG. 33. It is in the form of a tether 118 that is attached to the mouth guard 10, 12, 14 through the hole 210 in the handle 100. Multiple other means of retaining a mouth guard and preventing its loss are known in the literature, such as strings, elastic bands, lanyards or integral straps, which may be curved around an object and become attached to themselves. A lack of any illustration of these means of retaining a mouth guard should not be construed as limiting in any way to the present invention.

The maximum thickness of the moldable base member 20, that is the distance between the first and second non-planar biting surfaces 30, 40, is governed by certain practical limits, which are established by the maximum thickness that would be considered acceptable in the mouth of most persons, and by the limitations imposed by the thermoplastic material's ability to resist being bitten through. In some versions, the maximum thickness of the moldable base member 20 is no greater than about 4 mm in the posterior portion 60 or about 6 mm in the anterior portion 50. The moldable base member 20 is no thinner than necessary to prevent the thermoplastic material from being bitten through during use. This thickness will vary depending upon the type or grade of thermoplastic material that is employed in the fabrication of the mouth guard 10, 12, 14.

The moldable base member 20 has an average anterior thickness of from about 1 mm to about 5 mm and an average posterior thickness of from about 0.5 mm to about 4 mm with a gradual decrease in thickness from the anterior portion 50 to the posterior portion(s) 60.

In versions suitable for younger children, the moldable base member 20 is slightly thinner. The handle 100 and the anterior potion 50 of the moldable base member 20 can be of the same uniform thickness, which is from about 1 mm to about 5 mm, since the moldable base member 20 may vary in thickness along its length. Certainly, variations between the thicknesses of the handle 100 and the anterior portion 50 are considered acceptable and are within the scope of the expectations of the present invention.

One material that can be used for the present invention is a copolymer of ethylene and vinyl acetate (EVA). "ELVAX 240"® has a glass transition temperature between 100° and 120° F. and is marketed under the trademark "Elvax"® as a trademark of the E. I. Du Pont de Nemours Co., Wilmington, Del., 19898. There are many other compositions that are considered acceptable and within the following description of thermoplastic materials.

The mouth guard 10, 12, 14 is made of a thermoplastic that becomes moldable at a glass transition temperature that is greater than the temperature in the user's mouth. In one version, the mouth guard 10, 12, 14 is made from a thermoplastic having a glass transition temperature greater than about 95 degrees Fahrenheit. In another version, the thermoplastic becomes suitable for molding the mouth guard 10, 12, 14 to a user's upper and lower teeth 240, 250 at a temperature less than about 180 degrees Fahrenheit. A thermoplastic with a glass transition temperature greater than 180 degrees Fahrenheit could be used to form the mouth guard 10, 12, 14 of the present invention, provided that the mouth guard 10, 12, 14 is fitted to dental models of the person's teeth while the thermoplastic is in the moldable state and allowed to cool prior to use as a protective device. Examples of suitable thermoplastics include, but are not limited to, ethylene vinyl alcohol, ethylene vinyl acetate, urethane, styrene block copolymer, rubber, polystyrene, polybutadiene, polyisoprene, polyolefin, organopolysiloxane, alicyclic saturated hydrocarbon resin, polycaprolactone, polyethylene, unfilled polycarbonate, ester gum, polyethylenetetraphthalate, terpolymer, nylon, nylon copolymer, polyester, copolyester, or any combination of one or more thereof.

The thermoplastic can further comprise at least one non-toxic thermochromic element to provide the mouth guard 10, 12, 14 with a first color at less than the temperature in the user's mouth. In one version, the first color is displayed when the mouth guard 10, 12, 14 is at less than 100 degrees Fahrenheit. In another version, a thermochromic element causes a second color when the mouth guard 10, 12, 14 is at a temperature greater than about 95 degrees Fahrenheit. In another version, a third color is displayed at a temperature that is greater than the glass transition temperature of the thermoplastic. In another version, a thermochromic element provides the mouth guard 10, 12, 14 with a fourth color at a temperature greater than about 175 degrees Fahrenheit. Any one of the above colors or colored states of a thermochromic element may include 'colorless', or the absence of color, as a color option.

An exemplary mouth guard includes a moldable base member having first and second non-planar biting surfaces for positioning between occlusal surfaces of a user's upper and lower teeth, the moldable base member having an anterior portion, a posterior portion, a labial-buccal side and a lingual side with at least one moldable flange extending superiorly or inferiorly from either the labial-buccal side or the lingual side of the base member. The moldable flange shaped to form a barrier between the teeth and the soft oral tissue of a user. The moldable base member includes a shape to receive at least a portion of a user's teeth. The mouth guard includes the moldable base member having a generally semi-arcuate shape conforming to the arch form of a user's jaws to receive substantially all of the user's upper and lower teeth on at least one side of the user's mouth. An embodiment includes the moldable base member having a generally arcuate shape conforming to the arch form of a user's jaws to receive substantially all of the user's upper and lower teeth.

The exemplary mouth guard includes a handle having a distal end and a proximate end, the proximate end extending from the moldable base member and the distal end adapted to extend out of the user's mouth. Embodiments include the handle extending from the anterior portion or the posterior portion of the moldable base member. Embodiments include the handle extending from the lingual side of the moldable base member or from the labial-buccal side of the moldable base member.

Certain embodiments include a handle having a distal end and a proximate end, the proximate end extending from a moldable flange and the distal end adapted to extend out of the user's mouth. Embodiments include the handle extending from the anterior portion or the posterior portion of the moldable base member. Embodiments include the handle extending from the lingual side of the moldable base member or from the labial-buccal side of the moldable base member.

In certain embodiments, the moldable base member includes a plurality of cross-sectional shapes. In various embodiments, the moldable base member includes a sinusoidal or wave-like cross-section, a generally 'X'-shaped cross-section, and/or a generally circular solid elevational cross-section. The exemplary moldable base member and the moldable flange include at least one cavity.

In certain embodiments, the first and second non-planar biting surfaces include a plurality of cross-sectional shapes. Examples of the first and second non-planar biting surfaces include both surfaces having a generally concave cross-sectional shape, both surfaces having a generally convex cross-sectional shape, and a first non-planar biting surface having a generally convex cross-sectional shape and the second non-planar biting surface having a generally concave cross-sectional shape between the labial-buccal and lingual sides of the moldable base member.

Certain embodiments include the first and second non-planar biting surfaces having a plurality of deformations. In certain embodiments, the moldable flange extends from the anterior portion, the posterior portion, or both the anterior and posterior portions of the moldable base member in a generally perpendicular direction to the first and second non-planar biting surfaces.

In certain embodiments, the moldable flanges are shaped to conform to a plurality of frenae in a user's mouth. The moldable flanges may be shaped to conform to the labial-buccal frenae of a user's mouth, the lingual frenae of a user's mouth, the maxillary frenae of a user's mouth, and/or the mandibular frenae of a user's mouth.

In certain embodiments, the base member and the flanges include a thermoplastic adapted to be moldable at a temperature that is greater than the temperature in the user's mouth. Exemplary thermoplastics include a thermoplastic having a glass transition temperature greater than about 100 degrees Fahrenheit, and a thermoplastic adapted for molding to a user's teeth and soft oral tissues at a temperature less than about 180 degrees Fahrenheit. The thermoplastic may be ethylene vinyl alcohol, ethylene vinyl acetate, urethane, styrene block copolymer, rubber, polystyrene, polybutadiene, polyisoprene, polyolefin, organopolysiloxane, alicyclic saturated hydrocarbon resin, polycaprolactone, polyethylene, unfilled polycarbonate, ester gum, polyethylenetetraphthalate, terpolymer, nylon, nylon copolymer, polyester, copolyester, and/or combinations thereof.

In certain embodiments, the mouth guard includes a first non-toxic thermochromic element that provides the mouth guard with at least a first color at less than about 100 degrees Fahrenheit and that provides the mouth guard with a second color at more than about 95 degrees Fahrenheit or more than about 100 degrees Fahrenheit. The mouth guard further includes a third thermochromic element that provides the mouth guard with a third color at about a temperature greater than the temperature at which the thermoplastic becomes adaptable for molding, and/or a fourth thermochromic element that provides the mouth guard with a fourth color at more than about 180 degrees Fahrenheit.

In certain embodiments, the mouth guard includes a size adjusting means. Examples of the size adjusting means includes a hole, a partial depth cut, a slit, a slot, a scoring line, an intermittent perforation, and/or an interrupted perforation. In certain embodiments, the size adjusting means includes visual markings, raised ridges, lines, and/or dots, and the size adjusting means may be structured to aid in the process of adjusting the size of the mouth guard.

In certain embodiments, the mouth guard includes a means for assisting in placement and positioning of the mouth guard and confirming positioning of the mouth guard in the user's mouth. Examples of the means for assisting in placement and positioning of the mouth guard include means for retaining the mouth guard within the possession of the user and preventing loss of the mouth guard, and/or means for assisting in repositioning of the mouth guard and confirming repositioning of the mouth guard in the user's mouth.

In certain embodiments, the mouth guard includes a means for retaining a flavoring substance releasable into a user's mouth, and/or a means for retaining a medicating substance releasable into a user's mouth.

Another exemplary mouth guard includes a moldable base member, having a first non-planar biting surface and a second non-planar biting surface, for positioning between occlusal surfaces of a user's teeth, the moldable base member having an anterior portion, a posterior portion, a labial-buccal side and a lingual side. The mouth guard includes a thermoplastic, where the thermoplastic includes at least a first non-toxic thermochromic element. The moldable base member includes a shape to receive at least a portion of a user's teeth and a handle having a distal end and a proximate end, where the proximate end extends from the mouth guard and the distal end extends out of the user's mouth.

In certain embodiments, the proximate end of the handle extends from an anterior portion of the moldable base member, from a posterior portion of the moldable base member, from an anterior moldable flange, from a posterior moldable flange, from a labial-buccal moldable flange, and/or from a lingual moldable flange.

Another exemplary mouth guard includes a moldable base member, having a first non-planar biting surface and a second non-planar biting surface, for positioning between occlusal surfaces of a user's teeth, the moldable base member having an anterior portion, a posterior portion, a labial-buccal side and a lingual side. The mouth guard is made of a thermoplastic, where the thermoplastic includes at least a first non-toxic thermochromic element. The moldable base member includes a generally semi-arcuate shape conforming to the arch form of a user's jaws to receive substantially all of the user's teeth on at least one side of the user's mouth, and a handle having a distal end and a proximate end, where the proximate end extends from the mouth guard and where the distal end extends out of the user's mouth.

Yet another exemplary mouth guard includes a moldable base member, having a first non-planar biting surface and a second non-planar biting surface, for positioning between occlusal surfaces of a user's teeth, the moldable base member having an anterior portion, a posterior portion, a labial-buccal side and a lingual side. The mouth guard is made of a thermoplastic, where the thermoplastic includes at least a first non-toxic thermochromic element. The moldable base member includes a generally arcuate shape conforming to the arch form of a user's jaws to receive substantially all of the user's teeth and a handle having a distal end and a proximate end, where the proximate end extends from the mouth guard and where the distal end extends out of the user's mouth.

Specific embodiments of the disclosed invention have been shown and described for the purpose of illustration. It will be obvious to one possessing ordinary skill in the art that variations of the embodiments can be used and that the claimed invention can be practiced other than as described herein. The protection offered by any patent which may issue upon this application is not limited to the disclosed embodiments. Rather, the protection extends to all structures, arrangements and processes falling fairly within the scope of the claims appended hereto.

What is claimed is:
1. A mouth guard, comprising:
a moldable base member having first and second biting surfaces for positioning between occlusal surfaces of a user's upper and lower teeth;
the moldable base member having an anterior portion, a posterior portion, a labial-buccal side and a lingual side;

the moldable base member having a moldable flange extending in one of a superior or inferior direction from the moldable base member, and the moldable flange extending from one of the labial-buccal side or the lingual side of the moldable base member;

the moldable flange shaped to form a barrier between the teeth and the soft oral tissue of a user, and wherein the moldable flange comprises a frenal notch structured to conform to at least one frenum in the user's mouth; and a handle at the front of the mouth guard, the handle structured to protrude from the mouth of the user a distance sufficient for a caretaker to adjust a position of the mouth guard without placing fingers into the mouth of the user, wherein the handle further comprises visual markings structured to allow for proper alignment and positioning of the mouth guard in the user's mouth.

2. A mouth guard, comprising:

a moldable base member having first and second biting surfaces for positioning between occlusal surfaces of a user's upper and lower teeth;

the moldable base member having an anterior portion, a posterior portion, a labial-buccal side and a lingual side;

the moldable base member having a moldable flange extending in one of a superior or inferior direction from the moldable base member, and the moldable flange extending from one of the labial-buccal side or the lingual side of the moldable base member; and the moldable flange shaped to form a barrier between the teeth and the soft oral tissue of a user, and wherein the moldable flange comprises a frenal notch structured to conform to at least one frenum in the user's mouth, wherein the moldable flange comprises a labial-buccal flange, and wherein the labial-buccal flange comprises visual markings structured to allow for proper alignment and positioning of the mouth guard in the user's mouth.

3. A mouth guard, comprising:

a moldable base member having first and second biting surfaces for positioning between occlusal surfaces of a user's upper and lower teeth, wherein the moldable base member comprises at least one cross-sectional shape selected from the shapes consisting of: a sinusoidal cross-section, a wave-like cross-section, a generally circular solid elevational cross-section, and a plurality of cross-sectional shapes;

the moldable base member having an anterior portion, a posterior portion, a labial-buccal side and a lingual side;

the moldable base member having a moldable flange extending in one of a superior or inferior direction from the moldable base member, and the moldable flange extending from one of the labial-buccal side or the lingual side of the moldable base member; and the moldable flange shaped to form a barrier between the teeth and the soft oral tissue of a user, and wherein the moldable flange comprises a frenal notch structured to conform to at least one frenum in the user's mouth.

4. A mouth guard, comprising:

a moldable base member having first and second biting surfaces for positioning between occlusal surfaces of a user's upper and lower teeth wherein the moldable base member comprises an 'X'-shaped cross-sectional shape;

the moldable base member having an anterior portion, a posterior portion, a labial-buccal side and a lingual side;

the moldable base member having a moldable flange extending in one of a superior or inferior direction from the moldable base member, and the moldable flange extending from one of the labial-buccal side or the lingual side of the moldable base member; and the moldable flange shaped to form a barrier between the teeth and the soft oral tissue of a user, and wherein the moldable flange comprises a frenal notch structured to conform to at least one frenum in the user's mouth.

5. A method, comprising:

providing a mouth guard comprising a moldable base member having first and second biting surfaces for positioning between occlusal surfaces of a user's upper and lower teeth, the moldable base member having an anterior portion, a posterior portion, a labial-buccal side and a lingual side, the moldable base member having a moldable flange extending in one of a superior or inferior direction from the moldable base member, and the moldable flange extending from one of the labial-buccal side or the lingual side of the moldable base member, and the moldable flange shaped to form a barrier between the teeth and the soft oral tissue of a user, and wherein the moldable flange comprises a frenal notch structured to conform to at least one frenum in the user's mouth; and positioning the mouth guard into the user's mouth, wherein the positioning is performed by a caretaker that is not the user, the method further comprising positioning the mouth guard with a handle at the front of the mouth guard, and checking a visual marking on the mouth guard to verify a position of the mouth guard.

6. The method of claim 5, wherein the checking comprises checking that the visual marking is aligned with a philtrum of the user.

\* \* \* \* \*